(12) United States Patent
Bengmark et al.

(10) Patent No.: US 8,461,104 B2
(45) Date of Patent: Jun. 11, 2013

(54) SURFACE PROTECTION OF EXPOSED BIOLOGICAL TISSUES

(75) Inventors: Stig Bengmark, Höganäs (SE); Kåre Larsson, Bjärred (SE); Björn Lindman, Lund (SE); Roland Andersson, Lund (SE)

(73) Assignee: Bioactive Polymers AB, Lund (SE)

( * ) Notice: Subject to any disclaimer, the term of this patent is extended or adjusted under 35 U.S.C. 154(b) by 202 days.

(21) Appl. No.: 12/822,809

(22) Filed: Jun. 24, 2010

(65) Prior Publication Data

US 2010/0260822 A1 Oct. 14, 2010

Related U.S. Application Data

(62) Division of application No. 10/585,159, filed as application No. PCT/SE2004/002016 on Dec. 23, 2004, now abandoned.

(60) Provisional application No. 60/606,130, filed on Sep. 1, 2004.

(30) Foreign Application Priority Data

Dec. 30, 2003 (SE) ........................................ 0303588

(51) Int. Cl.
*C07K 4/00* (2006.01)
(52) U.S. Cl.
USPC .......... 514/1.1; 514/21.5; 514/21.6; 514/21.7
(58) Field of Classification Search
USPC ................................. 514/1.1, 21.5, 21.6, 21.7
See application file for complete search history.

(56) References Cited

U.S. PATENT DOCUMENTS

| | | | |
|---|---|---|---|
| 3,664,939 A | 5/1972 | Luner et al. | |
| 3,901,780 A | 8/1975 | Denckla | |
| 3,915,839 A | 10/1975 | Rilbe et al. | |
| 4,204,929 A | 5/1980 | Bier | |
| 4,378,224 A | 3/1983 | Nimni et al. | |
| 4,994,277 A | 2/1991 | Higham et al. | |
| 5,246,707 A | 9/1993 | Haynes | |
| 5,366,964 A | 11/1994 | Lindstrom et al. | |
| 5,409,904 A | 4/1995 | Hecht et al. | |
| 5,500,412 A * | 3/1996 | Carney et al. | 514/9.4 |
| 5,851,994 A * | 12/1998 | Schreiber et al. | 514/9.4 |
| 6,235,313 B1 | 5/2001 | Mathiowitz et al. | |
| 6,794,490 B2 * | 9/2004 | Hill et al. | 530/317 |
| 7,101,947 B2 | 9/2006 | Schlenoff et al. | |
| 7,671,011 B2 * | 3/2010 | Shai et al. | 514/1.1 |
| 2003/0087111 A1 | 5/2003 | Hubbell et al. | |

FOREIGN PATENT DOCUMENTS

| | | |
|---|---|---|
| EP | 0 705 878 A2 | 4/1996 |
| WO | WO 90/10031 | 9/1990 |
| WO | WO 97/07833 | 3/1997 |
| WO | WO 97/22371 | 6/1997 |
| WO | WO 99/03481 | 1/1999 |

OTHER PUBLICATIONS

Storm (Annual Review of Biochemistry 46, 723-763, 1977).*
"Isoelectric Focusing, Principles and Methods." pp. 128-129 (Pharmacia Fine Chemicals, Uppsala, Sweden 1982.).
Elbert et al. "Reduction of fibrous adhesion formation by a copolymer possessing an affinity for anionic surfaces." *Journal of Biomedical Material Research*. vol. 42, 1998. pp. 55-65.

* cited by examiner

*Primary Examiner* — David Lukton
(74) *Attorney, Agent, or Firm* — Merchant & Gould P.C.

(57) ABSTRACT

The invention relates to a biodegradable barrier network comprising at least two polypeptides, one being anionic and the other one cationic. The invention also relates to applicators and kits comprising components to be used to create said biodegradable barrier network. The invention also relates to the use of said applicator or kit in therapy, such as in medicine, veterinary medicine and horticulture.

16 Claims, No Drawings

SURFACE PROTECTION OF EXPOSED BIOLOGICAL TISSUES

This application is Divisional of U.S. Ser. No. 10/585,159, filed 19 Apr. 2007, now abandoned, which is a National Stage Application of PCT/SE2004/002016, filed 23 Dec. 2004, which claims benefit of Ser. No. 0303588-8, filed 30 Dec. 2003 in Sweden and U.S. Ser. No. 60/606,130, filed 1 Sep. 2004 and which applications are incorporated herein by reference. To the extent appropriate, a claim of priority is made to each of the above disclosed applications.

FIELD OF INVENTION

The invention relates to a biodegradable barrier network comprising two polypeptides, one being anionic and the other one cationic. The invention also relates to applicators and kits comprising components to be used to create said biodegradable barrier network. The invention also relates to the use of said applicator or kit in therapy, such as in medicine, veterinary medicine and horticulture.

BACKGROUND OF INVENTION

Tissue surfaces need protection depending on the type and extent of chemical exposure and wearing that they normally are subjected to. All cells in the body are thus covered by a cell membrane bilayer that mainly consists of lipids and proteins. Epithelial surfaces, which connect to the exterior world; the respiratory, gastrointestinal, and to some extent also the genitourinary tracts, are exposed to a rather harsh environment. These epithelial surfaces are further covered by a mucus layer having viscoelastic and pronounced protecting properties. Tissues such as synovia and mesothelium, on the other hand, are not protected by mucus since they are not exposed to drastic condition of the same magnitude.

In addition, the vital epithelial tissues, such as blood vessels or blood organs, are coated with mucous, serous, synovial and endothelial membranes so that they can function independently of each other. The peritoneal, pericardial and pleural membranes consist of a single layer of mesothelial cells, which is covered by a thin film of peritoneal fluid. The components of the membranes as well as the covering layer of fluid have several functions, e.g. lubrication of the enclosed organs.

The protective epithelial membrane is very thin and comprises a delicate layer of connective tissue covered with a monolayer of mesothelial cells and only one or a few bilayers of phospholipids. This makes the synovia and mesothelium tissue especially vulnerable to infection and trauma. When such a membrane is exposed to a physical, chemical or microbial challenge, many potent substances, which are harmful to the membrane, are often released in response thereto. The structure and function of the membrane is consequently easily destroyed in connection with trauma, ischemia, and infection. After an irritation of the stress-sensitive membrane, e.g. only by the desiccation or abrasion of the membrane surfaces during surgery, it will rapidly be covered with a fibrin clot. Since the plasminogen activating activity (i.e. the fibrinolytic capacity) is reduced after trauma, the fibrin clots will later on become organised as fibrous adhesions, i.e. small bands or structures, by which adjacent serous or synovial membranes adhere in an abnormal way. Surgical operations, infection or inflammation in those parts of the body, which are coated with serous or synovial membranes, can result in adhesive inflammation regardless of the size of the affected area. The adhesions between vital epithelial tissues are formed within the first few days following surgery trauma or infection and may be observed not only in particular portions of the body but in all vital tissues. Such adhesions between for example contact zones between intestines or between intestines and the abdominal wall are the result of the often unnoticed tissue damage as desiccation and they occur for various reasons, including mechanical and chemical stimulation of vital tissues accompanying surgical manipulations, postoperative bacterial infection, inflammation or further complications.

Adhesion of vital epithelial tissues, large or small, may be observed in most surgical fields. It has been reported that of all patients undergoing abdominal surgery at one hospital over a four-year period, 93% were found to have adhesions from previous operations. In addition, in a 10 year period there will be a need of adhesion prevention in about 20% of all surgical operations, which corresponds to more than 1 million operations annually on each major continent.

However, the obtained postsurgical adhesions are the result of a natural wound healing response of tissue damage occurring during surgery. Numerous factors play a role in peritoneal wound healing and the development of adhesions. Among others are peritoneal macrophages known to have an important role in initial peritoneal repair.

Thus, while waiting after surgery for the body to produce new protective layers it is desired to supply the corresponding protection from the outside to exposed epithelial surfaces in an effective way. Furthermore, it is important to prevent or reduce the infection and/or the inflammation obtained after surgery as well as the accompanying fibrin formation.

Various bioactive materials and macromolecules have been reported to decrease the extent of postoperative abdominal adhesions. Likewise, a number of methods for limiting the formation of surgical adhesion have been studied with some encouraging but often ambiguous results. However, most efforts made to avoid or reduce postoperative peritoneal adhesions have finally been abandoned. Among the methods used prevention of fibrin formation, reduction of fibrin formation, surface separation, and surgical techniques can be mentioned.

Numerous investigations have been carried out in which barriers are placed at a site of injury in order to prevent fibrin bridge formation between the injured tissue and neighboring organs. Such barriers include resorbable materials, such as enzymatically degradable oxidized regenerated cellulose, and slowly dissolving physiochemically crosslinked hydrogels of the Pluronic™ type.

Most methods of surface protection of exposed epithelial surfaces, whereby a postsurgical adhesion formation is limited, have also focused on providing wound separation by placing a material between the tissues. In addition, several types of viscous polymer solutions such as polyvinylpyrrolidone, sodium carboxymethyl cellulose, dextrans, and hyaluronic acid have been added before and/or at the end of surgery in order to control the wound healing events after the occurrence of the presumed tissue injuries. These solutions are supposed to act by increasing the lubrication and preventing the fibrin clots from adhering to other surfaces or by mechanically separating damaged tissues while they heal.

The employed polymeric solutions are mainly based on the viscosity of the high molecular weight polymer, which is intended to increase with increasing concentration. The polymer is often a polysaccharide as in U.S. Pat. No. 4,994,277, in which a viscoelastic gel of biodegradable xanthan gum in a water solution for preventing adhesions between vital tissues is described. However, the major disadvantage of these polymers, when used for reducing for example peritoneal adhesions as protective coatings during surgery or surface separation agents after surgery, is that they do not significantly reduce adhesions because of their short residence time in the peritoneal cavity. The result is that subsequent surgeries have to be performed on the patient.

Less viscous polymer solutions have been used as a tissue protective coating during surgery in order to maintain the natural lubricity of tissues and organs and to protect the enclosing membrane. Precoating for tissue protection and adhesion prevention includes coating tissues at the beginning of surgery before a significant tissue manipulation and irritation can occur and continuously throughout the operation so that a protective coating can be maintained on the tissues.

U.S. Pat. No. 5,366,964 shows a surgical viscoelastic solution for promoting wound healing, which is used in direct contact with cells undergoing wound healing. The solution is intended for cell protection and cell coating during surgery and comprises one or several polymeric components. Hydroxypropylmethyl cellulose and chondroitin sulphate are supposed to lubricate the tissue, while sodium hyaluronate would provide viscoelastic properties to the solution.

Several agents of today for treating postsurgical adhesions contain hyaluronic acid. For example U.S. Pat. No. 5,409,904 describes solutions which reduce cell loss and tissue damage intended for protecting endothelial cells during ophthalmic surgery. The compositions used are composed of a viscoelastic material comprising hyaluronic acid, chondroitin sulphate, modified collagen, and/or modified cellulose. In WO 9010031 a composition is described for preventing tissue adhesion after surgery containing dextran and hyaluronic acid in which the substances are supposed to act synergistically. In WO 9707833 a barrier material for preventing surgical adhesions is shown, which comprises benzyl esters or covalently crosslinked derivatives of hyaluronic acid.

A hyaluronic acid based agent manufactured by Pharmacia under the trademark Healon and originally intended as an intraocular instillation has been found to be the most effective agent up to now. However, hyaluronic acid is isolated from cock's crests and is thus very expensive as well as potentially allergenic even in small quantities and even more for large surfaces such as the peritoneum which has an area of about two $m^2$.

In WO 9903481 a composition for lubricating and separating tissues and biological membranes from adjacent membranes or adjacent cells or tissues is shown, which comprises a hydrophobic polymer formed from a biologically acceptable water-soluble cationic polymer carrying covalently bound hydrophobic groups.

Likewise, water-insoluble biocompatible compositions are shown in EP 0,705,878, which comprise a polyanionic polysaccharide combined with a hydrophobic bio-absorbable polymer.

In U.S. Pat. No. 6,235,313 a variety of polymers were compared for adhesive force to mucosa surfades. Negatively charged hydrogels, such as alginate and carboxymethyl cellulose, with exposed carboxylic groups on the surface, were tested, as well as some positively-charged hydrogels, such as chitosan. The choice was based on the fact that most cell membranes are actually negatively charged. However, there is still no definite conclusion as to what the most important property is in order to obtain good bioadhesion to the wall of the gastrointestinal tract. For example, chitosan is considered to bind to a membrane by means of ionic interactions between positively charged amino groups on the polymer and negatively charged sialic acid groups on the membrane. Thus, polycationic molecules, such as chitosan and polylysine, have a strong tendency to bind to exposed epithelial surfaces since these generally have a negative net charge.

A main drawback of both these cationic molecules is that they exhibit toxic effects. For example, polylysine is considered to act as an inhibitor of the calcium channel by producing a conformational change, thereby inhibiting transmembrane ion fluxes.

SUMMARY OF THE INVENTION

The invention relates to a new invented biodegradable barrier network, which is non-toxic, which is possible to produce at low cost, biodegradable and non-allergenic. Such a network enables the possibility to treat postsurgical adhesions in an efficient way.

First, the invention relates to an biodegradable barrier network comprising a cationic polypeptide, an anionic polypeptide and a pharmaceutically acceptable carrier.

Secondly, the invention relates to an applicator comprising a cationic polypeptide and a pharmaceutically acceptable carrier, an anionic polypeptide and a pharmaceutically acceptable carrier, said cationic and anionic peptide being separated from each other by a separator.

Thirdly the invention relates to a kit comprising a cationic polypeptide and a pharmaceutically acceptable carrier an anionic polypeptide and a pharmaceutically acceptable carrier and means for administering said cationic and anionic polypeptide.

Finally the invention relates to a method of treating a mammal having an injury, comprising use of the applicator or the kit according to the invention to create the biodegradable barrier network according to the invention.

By providing such a network, applicator and kits a new improved product will be available on the market to be used in wound healing.

DETAILED DESCRIPTION OF THE INVENTION

Definitions

In the context of the present invention the following definitions apply:

The term "biodegradable barrier network" is intended to mean a barrier, which prevent adhesion between tissues at an injury and to provide protection of an injured tissue against for example inflammation and infectious agents. Additionally the barrier is degradable over time during the healing process of the injury.

The "network" is intended to mean a network formed between a mixture of at least two polypeptides, where at least one is cationic and the other one anionic.

The "same type of amino acid residue" is intended to mean that amino acid residues in a polypeptide is for example solely H (H-H-H-H-H-H).

In the present context, amino acid residue names are used as defined by the Protein DataBank (PNB) (www.pdb.org), which is based on the IUPAC nomenclature (IUPAC Nomeclature and Symbolism for Amino Acids and Peptides), Eur J Biochem., 138, 9-37 (1984) together with their corrections in Eur J Biochem., 152, 1 (1985). The term "amino acid" is intended to indicate an amino acid from the group consisting of arginine (Arg, or R), histidine (His or H), lysine (Lys or K), aspartate (Asp or D) and glutamate (Glu or E)

The Biodegradable Barrier Network

The invention relates to a biodegradable barrier network. The biodegradable barrier network being produced at sites of injury. The network, comprising a cationic polypeptide an anionic polypeptide and a pharmaceutically acceptable carrier. The network, being formed by applying at least one anionic and at least one cationic polypeptide in sequence to a tissue. The cationic polypeptide carrier gelled in order to focus its administration. The tissue being injured and the protecting membrane party or totally removed. Thereby the underlying tissue being exposed and the network will serve as protection of the exposed epithelian surfaces of a mammal, such as humans or animals.

The cationic polypetide may be selected from the group consisting of amino acid residues R, H, K, synthetic and semisynthetic variants and mixtures thereof, such as being a poly-lysine, poly-arginine or poly-histidine. The polypeptide may be in the L form. The polypeptide may be a polypeptide consisting of one and the same amino acid residue, such as R-R-R-R or H-H-H-H or a mixture thereof, such as R-H-R-R-H etc. One or more synthetic or semisynthetic amino acid residues may also be present in the polypeptide.

The anionic polypeptide may be selected from the group consisting of the amino acid residues D, E, synthetic and semisynthetic variants, such as being a poly-glutamate or poly-aspartate. The polypeptide may be in the L-form. The polypeptide may be a polypeptide consisting of one and the same amino acid residue, such as D-D-D-D or E-E-E-E or a mixture thereof, such as D-D-E-D-E. One or more synthetic or semisynthetic amino acid residues may also be present in the polypeptide.

The length of the polypeptides may be the same or different, depending on where the biodegradable barrier network should be formed, i.e., depending on which tissue it should be applied to. The size may be at least 5,000 Da, such as between about 5,000 to about 50,000 Da. Examples are 6,000, 7,000, 8,000, 10,000, 15,000, 20,000, 30,000, 40,000 and mixtures thereof.

Additionally, at least one of the above mentioned polypeptides may be linked to at least one different neutral amino acid residue, other peptides or other substances, such as a substance which cleans the injured surfaces, provides antioxidants, modulates apoptosis, promotes healing, inhibits fibrogenesis and tumour growth, controls bleeding, inhibits inflammation, increases stability or protects against infection. Examples are antimicrobial agents, antiinflammatory agents, cleaning agents, antioxidants, apoptosis modulators, healing agents, fibrogenesis inhibitors, antitumor agents and antibleeding agents.

Accordingly the polypeptides may be modified by amidation, esterification, acylation, acetylation, PEGylation or alkylation.

The above mentioned network may also comprise a pharmaceutical acceptable diluent or buffer.

"Pharmaceutically acceptable carrier" means a non-toxic substance that does not interfere with the effectiveness of the surface protection activity of the polypeptides. Such acceptable buffers or diluents are well-known in the art (see Remington's Pharmaceutical Sciences 18$^{th}$ edition, A. R Gennaro, Ed., Mack Publishing Company (1990).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO, TES, tricine.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The invented network may also comprises one or more therapeutic agent such as an antimicrobial, antiinflammatory agent, substances which cleans the injuried surfaces, provides antioxidants, modulates apoptosis, promotes healing, inhibits inhibits fibrogenesis and tumour growth or controls bleeding.

Examples of therapeutic agents are penicillins, ephalosporins, carbacephems, tetracyclines, macrolides, iodine, silver, copper, clorhexidine, acetylsalicylic acid and examples of cleaning substances are proteolytic enzymes.

Examples of agents having antioxidant activity are various vitamins, glutathione, folic acid, curcumin, resveratrol, epigallocathechin, anthocyanidins and numerous other agents.

Examples of agents which modulates apoptosis, inhibits fibrogenesis and tumour growth are glucocorticosteroids, insulin, dexamethasone, carotenoids, linoleic and conjugated-linoleic acids, melatonin, isothiocyanates, shikonin, solamargine, perifosine, deoxynivalenol, carboxyamido-triazole (CAI), histone deacetylase inhibitors and numerous other agents.

Examples of agents which promotes healing are various growth factors, insulin, vitamin E, retinoic acid, herbal components and numerous other agents and examples of agents which controls bleeding are norepinephrine, gelatin, collagen, oxidized cellulose and numerous other agents.

The above mentioned polypeptide can be synthesised by standard chemical methods including synthesis by automated procedure. In general, peptide analogues are synthesised based on the standard solid-phase Fmoc protection strategy with HATU (N-[DIMETHYLAMINO-1H-1.2.3.-TRIAZOLO[4,5-B]PYRIDIN-1-YLMETHYLELE]-N-METHYLMETHANAMINIUM HEXAFLUOROPHOSPHATE N-OXIDE) as the coupling agent or other coupling agents such as HOAt-1-HYDROXY-7-AZABENZOTRIAZOLE. The peptide is cleaved from the solid-phase resin with trifluoroacetic acid containing appropriate scavengers, which also protects side chain functional groups. Crude peptide is further purified using preparative reversed-phase chromatography. Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides.

An Applicator or Kit of the Invention

Additionally, the invention relates to an applicator comprising a cationic polypeptide and a pharmaceuticaly acceptible carrier, an anionic polypeptide and a pharmaceutically acceptable carrier, said cationic and anionic polypeptide being separated from each other by a separator. The polypeptides being as defined above and the solution is a pharmaceutically acceptable solution as defined above.

The applicator may be syringes, one or two component sprays, nebulators, plasters, catheters, adhesives, implants and bandages.

The separator separating the anionic and the cationic polypeptide prior to that they are applied to an injured tissue may be any separator as long as it is non-toxic and does not influence the effect of the polypeptides. The separator may be biodegradable. The main function of a separating layer between the two polypeptide solutions is to wash out all of the cationic peptide before administration of the polyanionic one and to avoid precipitation already in the applicator. It should therefore only consist of distilled water or the buffer used in solution of the polypeptides. However, this water solution should not dilute the polypeptide solutions and should therefore not be administrated on the first applied cationic polypeptide. The separator may be a gelled state of the aqueous solution. Additionally the separator may be a membrane.

Additionally, the applicator may comprise one or more therapeutic agents, such as those defined above. The agents, being (separated from the two polypeptides or) mixed with one or both of the polypeptides.

The therapeutic agent may be selected from the group consisting of penicillin, cephalosporin, carbacephems, tetracyclines, macrolides, iodine, silver, copper, clorhexidine and antiinflammatory agents such as acetylsalicylic acid.

Accordingly the invention relates to a kit comprising a cationic polypeptide and a pharmaceutically acceptable carrier, an anionic polypeptide and a pharmaceutically acceptable carrier and means for administering said cationic and anionic polypeptide. The polypeptides being as defined above.

The means may be selected from the group consisting of syringes, sprays, plasters, catheter, adhesives, implant and bandages.

Additionally the kit may comprise one or more therapeutic agent such as antimicrobial and antiinflammatory agents. Other suitable therapeutic agents are those defined above. The therapeutic agent is selected from the group consisting of penicillin, cephalosporin, carbacephems, tetracyclines, macrolides, iodine, silver, copper, clorhexidine and acetylsalicylic acid.

The therapeutic agent in the applicator or kit described above may be separated from the two polypeptides or mixed with one or both of the polypeptides.

The applicator and/or the kit as described above may be used in therapy, such as in medicine, veterinary and horticulture.

Finally the invention relates to a method of treating a mammal having an injury, comprising use of the applicator and/or the kit as described above, creating the disclosed network. Examples of areas in which the invention can be useful includes ophtalmic bulb injuries and infections, nasal wounds, injuries and infections, skin injuries and infections, sun burns, thermic skin injuries/burns, bed sores, chronic leg ulcers, vaginal wounds, urinary bladder inflammation, oesophageal and stomach ulcers, inflammation and ulcers of the intestine, inflammations and serosal injuries of joints, cut surfaces or injuries to solid organs such as lung, liver and spleen, bone injuries, peritoneal defects and inflammation.

EXAMPLES

The invention will now be further described and illustrated by reference to the following examples. It should be noted, however, that these examples should not be considered as limiting the invention in any way.

Example 1

Adhesion Prevention

A reproducible and standardized rat and rabbit model was adopted. Forty eight female MRI mice weighing about 25-30 g were used to induce the adhesions and forty two for further tests. The animals were kept under standardized conditions and had free access to pellet and tap water.

Anesthesia was induced by ketamine 150 mg/kg (Ketalar, Parke Davis) and zylazine 7.5 mg/kg (Rompun, Bayer Sverige A B) intramuscular injection. After disinfection, a 25 mm long midline laparotomy was performed. Both peritoneal surfaces of the lateral abdominal wall were exposed, and 2×15 mm long sharp incisions were performed at the same distance from the midline, including the muscles. The wounds were immediately closed with 2×4 single sutures at equal distances by using 5.0 polypropylene (Prolene, Ethicon, Johnson & Johnson). The midline laparotomy was closed in two layers with a continuous 5.0 polypropylene suture. At the evaluation time an overdose of anesthetic was administered, the abdomen was totally opened through a U-shaped incision with its base to the right. The lengths of the adhesions were measured on both sides using a metal caliper, and data was expressed as percent wounds covered by adhesions.

Aqueous solutions of 0.5% poly-L-glutamate, and poly-L-lysine were freshly made on the day of the experiment and stored in refrigator until used. FITZ-labeled polylysine was mixed with polylysine in a proportion of 1:10 (wt). All chemicals and cell culture substrates were purchased from Sigma-Aldrich, St Louis, USA; fluorescent microparticles (Nile Blue Labeled) were bought from Microparticles GmbH., (Berlin, Germany).

The animals were divided randomly into 4 groups based on the treatment and the evaluation time. The control groups were intraperitoneally injected with 2 ml physiologic sodium chlorine solution. Two treatment groups received 1 ml poly-L-lysine solution and 5 min later 1 ml poly-L-glutamate solution. One of the control and treatment groups (2×14 animals) was sacrificed one week after surgery and the lengths of the adhesions were calculated. The remaining two groups (2×10 animals) were kept for four weeks before they underwent the evaluation process.

The Kruskal Wallis test was used to determine the difference in adhesion amount among the different treated groups and the Mann Whitney U test was used to compare the individual groups.

A significant decrease in adhesion development was detected both one week and one month after the peritoneal challenge (**$p \leq 0.001$) compared to the corresponding controls (Mann-Whitney U test). A marked (22%) though not significant ($p=0.235$) decrease was obtained after one month between the control groups, while there were no difference between the treated groups by that time.

No adhesions were found which were related to a heavy compound deposit in different locations from the wound itself. After 24 h, the animals that had been given both poly-L-lysine and poly-L-glutamate exhibited a massive protecting layer over the peritoneal wound, and thin film at the rest of peritoneal surface. However the FITZ-labeled compound was only visible in the wound one day later and was detectable both over and inside the wound. The deposit was gradually rebuilt until the end of the 6 day observation period.

Example 2

Phagocytosis and Particle Ingestion Index

The time course of the phagocyte function was tested in vitro on peritoneal resident macrophages from mice after 0.5 h, 1 h, 2 h, 3 h, 4 h, 5 h, 6 h, 8 h, 10 h, 12 h, 16 h, and 24 h incubation with poly-L-lysine+poly-L-glutamate (40 µg/ml) and/or fluorescent particles (1 µm).

Macrophage samples were taken by abdominal lavage with 10 ml ice cold DMEM-solution. The samples in medium were immediately centrifuged at 1200 rpm for 10 min. The cells were resuspended in DMEM containing 10% FBS and penicillin/streptomycin and then plated on 48 wells cell culture plates; $5 \times 10^5$ cells in each well. After 1.5 h non-adherent cells were washed away, particles (100/cell) together with test drugs (poly-L-lysine+poly-L-glutamate) were added in a dose of 40 μg/ml to 12×5 wells, and particles only were added to the remaining 12×5 wells. Moreover negative controls were performed at each time point. The cells were incubated (37° C., 5% $CO_2$) and detached and fixed at the evaluation time by using 250 μl 5 mM EDTA and an equal volume of 2% paraformaldehyde. FACS analysis (FACScan, Becton Dickinson, San Jose, Calif.) was made, when cell size (forward scatter, FSC), granularity (side scatter, SSC) and fluorescence intensity (in FL3 channels) were recorded of $1.5 \times 10^4$ cells in each measurement. In manually defined gates the ratio phagocyting cells/total macrophages was expressed in percent as mean of data from five wells at each time and treatment group (control and poly-L-lysine+poly-L-glutamate).

The non-treated cells incorporated more particles. Thus, the maximum plateau (median) level of their fluorescence intensity (FL3) and SSC was set as 100%. All measurements were expressed as the median percentage of the plateau level and termed particle ingestion index, since it refers to the amount of particles ingested.

The Mann Whitney U test was used to check the plateau of phagocytosis and the Wilcoxon Signed Ranks test was used to test the difference in the phagocytosis and particle ingestion index between the treatment pairs (control and poly-L-lysine+poly-L-glutamate, respectively).

While the phagocytosis index of the non-treated macrophages reached the plateau of phagocytosis about 5 h (the difference between 4 and 5 h decreased below the insignificant level, p=1), the treated population required 8 h for the same effect. (The difference between 8 and 10 h was insignificant, p=0.058). A low but significant (p=0.043) difference was obtained in the phagocytosis index after 24 h (97.3% and 94.3%, respectively).

The time course for the ingestion index, which refers to the number of particles phagocytosed by macrophages became significant between 1 and 2 h (p=0.008). The control cell population reached the plateau between 16 and 24 h (insignificant difference between the index at 12 and 24 h (p=0.841) while the treated cell population did not reach the plateau at all during the first 24 h studied. Furthermore, the number of ingested particles were significantly lower in the treated group at all times (p=0.043).

Flow cytometry verified that macrophages phagocyte the test compound particles, which resulted in significant cell growth and large phagocytic vacuoles.

Example 3

Transmission Electron Microscopy

Peritoneal macrophages were harvested from two healthy non-treated animals as described above and plated on cell culture plates (Thermanox, Naperville, Ill., USA). The cells were washed away after 1.5 h and poly-L-lysine+poly-L-glutamate (40 μg/ml) in supplemented DMEM solution were added in sequence followed by a 24 h incubation. The incubation medium was removed and the cells were fixed in 2.5% phosphate buffered glutaraldehyde was followed by rinsing in Milloning's phosphate solution. Samples were postfixed in 1% osmium tetroxide and subsequently dehydrated with graded series of ethanol, which was followed by embedding in Araldite 502 kit. Vertical sections were obtained with a diamond knife and stained with uranyl acetate and lead citrate in a LKB Ultrastainer. Samples were examined in a JEOL 1200 EX transmission electron microscope (TEM).

Electron microscopy verified that macrophages phagocyte the test compound particles, resulted in significant cell growth, and large phagocytic vacuoles.

Example 4

Scanning Electron Microscopy

Peritoneal swabs and wounds were taken from eight treated (4) and non-treated (4) animals after one and seven days of surgery and cell cultures Were conducted as above. The samples were fixed in 2.5% phosphate buffered glutaraldehyde at room temperature and then post-fixed in 1% $OsO_4$. The samples were dehydrated in acetone, critical point dried and sputter-coated with gold before being studied in a LEO 420 electron microscope.

SEM data showed that mesothelial cells covered the compound surface from the first day.

Example 5

Histology

Eight animals were opened and then injected intra-peritoneally with poly-L-lysine+poly-L-glutamate. At the postoperative first, second, third, and sixth days, two animals were sacrificed and the wounds were excised. They were rapidly frozen and embedded, and the block obtained was immediately cut into slices of 7 μm. The slices were allowed to dry in dark for 30 min at room temperature and were then stained with 100 μg/1 4'6'-diamino-2-phenylindole hydrochloride (DAPI) solution for 10 min. Fluorescent microscopy was performed with both a FITZ and a DAPI filter, and images were digitally merged (OpenLab, Improvosion). Macro photo was made about the excised wounds by using transillumination, mixed ambient room light, and UV illumination.

The histological studies showed that the added material was present in the wound from the first day. Furthermore, more and more cells were detected for each day until the matrix was completely rebuilt.

Example 6

Biodegradation

Healthy non-operated animals were treated intra-peritoneally as in Example 1 and sacrificed after two months.

No visible remains of poly-L-lysine and poly-L-glutamate could be detected. The biodegradability is supported by findings that at one month's follow up the same results were obtained by using a double dose of poly-L-lysine+poly-L-glutamate, although that caused some additional adhesions related to the compound at evaluation on the $7^{th}$ day.

Example 7

Biodegradation

Aqueous solutions of 1% and 2% lysozyme, poly-L-glutamate, poly-L-lysine, and poly-L-glutamate, and 0.25% of hyaluronic acid were freshly made. Solutions of lysozyme, polyglutamate, lysozyme+polyglutamate and polylysine+polyglutamate were then administered to animals as in Example 1.

The extent of abdominal adhesions one week after surgery significantly decreased in the four treated groups (p≦0.001) as compared to controls. However, no significant change in response was obtained with hyaluronic acid (p=0.264). The combinations poly-L-lysine/lysozyme seemed to result in an insoluble product.

Example 8

Effect of Poly-L-Lysine Alone

An aqueous solution of 0.5% poly-L-lysine was freshly made and administered to animals as in Example 1.

Such an administration of poly-L-lysine alone resulted in convulsions and death within 30 min, i.e. before they woke up from the anesthesia. The symptoms seemed to be related to the effect of opening calcium channels, plasma $Ca^{++}$ levels being rapidly decreased.

Outlay of the Experimental Procedure a. Standard thermic injuries were produced on the two sides of the back of ten mice. One wound was treated with the composition, the other served as control. Reduced rate of infection, faster healing and less sequelae were seen in the treated wounds.

b. One cm long incisions were done on each side of the back of ten rats. One incision was filled with the composition, the other served as control. Uneventful and faster healing was observed of the treated wound.

c. Standard incisions were done in both the liver and spleen of ten rats. Additional ten rats served as controls. The amount of bleeding was significantly reduced in the treated animals. The treatment glued together the defect, which resulted in a faster healing and less sequelae.

d. Colonic mucosa inflammation and wounds were induced in rats by several methods such as acetic acid infusion, methotrexate and dextran sulphate. The inflammatory surfaces and wounds were "painted" with the composition. Reduced inflammation and enhanced healing was observed.

e. Human nasal mucosa wounds and infections were treated with the composition. A fast cleansing of the wounds and healing was observed.

f. Human bed sores were treated by the composition. A fast cleansing of the infected and necrotic surfaces was observed. The treatment was repeated over a longer period of time.

g. Human chronic leg ulcers were treated by the composition, A fast cleansing of the infected and necrotic surfaces was observed. The treatment was repeated over a longer period of time.

The invention claimed is:

1. A method of treating a mammal having an injury, wherein said method comprises the steps of:
    a) applying a cationic polypeptide to said injury, the cationic polypeptide consisting of amino acid residues R, H, K or a combination thereof;
    b) applying an anionic polypeptide to said injury, the anionic polypeptide consisting of amino acid residues D, E, or a combination thereof;
    c) applying a pharmaceutically acceptable carrier to said injury; and
    d) forming a biodegradable barrier network at the site of said injury, wherein the cationic polypeptide interacts with the anionic polypeptide to form a biodegradable barrier network at the site of said injury that reduces adhesion between tissues;
    wherein said cationic polypeptide is added separately from said anionic polypeptide.

2. The method according to any claim 1, wherein the amino acid residues within at least one of the polypeptides comprise amino acid residues of the same type.

3. A method of treating a mammal having an injury, wherein said method comprises the steps of:
    a) applying a cationic polypeptide to said injury, the cationic polypeptide consisting of amino acid residues R, H, K or a combination thereof wherein the cationic polypeptide is optionally modified by carboxamidation, esterification, acylation, acetylation, PEGylation or alkylation;
    b) applying an anionic polypeptide to said injury, the anionic polypeptide consisting of amino acid residues D, E, or a combination thereof wherein the anionic polypeptide is optionally modified by carboxamidation, esterification, acylation, acetylation, PEGylation or alkylation;
    c) applying a pharmaceutically acceptable carrier to said injury; and
    d) forming a biodegradable barrier network at the site of said injury, wherein the cationic polypeptide interacts with the anionic polypeptide to form a biodegradable barrier network at the site of said injury that reduces adhesion between tissues;
    wherein said cationicpolypeptide is added separately from said anionic polypeptide.

4. The method according to claim 1, wherein the peptides have a size of at least 1,000 Da.

5. The method according to claim 1, wherein the pharmaceutically acceptable carrier comprises a diluent or buffer.

6. The method according to claim 1, wherein said method further comprises applying a therapeutic agent selected from the group consisting of antimicrobial agents, anti-inflammatory agents, cleaning agents, antioxidants, apoptosis modulators, healing agents, fibrogenesis inhibitors, antitumor agents and anti-bleeding agents.

7. The method according to claim 6, wherein the therapeutic agent is selected from the group consisting of penicillins, cephalosporins, carbacephems, tetracyclines, macrolides, iodine, silver, copper, clorhexidine, acetylsalicylic acid, proteolytic enzymes, vitamins, glutathione, folic acid, curcumin, resveratrol, epigallocathechin, anthocyanidins, glucocorticosteroids, insulin, dexamethasone, carotenoids, linoleic and conjugated-linoleic acids, melatonin, isothiocyanates, shikonin, solamargine, perifosine, deoxynivalenol, carboxyamidoriazole (CAI), histone deacetylase inhibitors, growth factors, insulin, vitamin E, retinoic acid, herbal components norepinephrine, gelatin, collagen and oxidized cellulose.

8. The method according to claim 1, wherein the method is performed by use of an applicator comprising:
    a) said cationic polypeptide;
    and a pharmaceutically acceptable carrier; and
    b) said anionic polypeptide and a pharmaceutically acceptable carrier;
    said cationic polypeptide and anionic polypeptide being separated from each other by a separator.

9. The method according to claim 8, wherein the applicator is selected from the group consisting of syringes, one or multi-component sprays, nebulators, plasters, catheters, adhesives, implants and bandages.

10. The method according to claim 8, wherein the separator is a gelled aqueous solution or a membrane.

11. The method-according to claim 6, wherein the therapeutic agent is applied separate separately from the cationic and the anionic polypeptides.

12. The method according to claim 6, wherein the therapeutic agent is applied with one or both of the polypeptides.

13. The method according to claim 1, wherein said injury is selected from the group consisting of ophtalmic bulb injuries and infections, nasal wounds, injuries and infections, skin injuries and infections, sun burns, thermic skin injuries/burns, bed sores, chronic leg ulcers, vaginal wounds, urinary bladder inflammation, oesophageal and stomach ulcers, inflammation and ulcers of the intestine, inflammations and serosal injuries of joints, cut surfaces or injuries to solid organs, bone injuries, peritoneal defects and inflammation.

14. The method according to claim 1, wherein the cationic polypeptide is a poly-lysine, poly-arginine, or poly-histidine.

15. The method according to claim 1, wherein the anionic polypeptide is a poly-glutamate or poly-aspartate.

16. The method according to claim 13 wherein said solid organs are selected from the group consisting of lung, liver and spleen.

* * * * *